(12) United States Patent
Hüttermann et al.

(10) Patent No.: US 7,777,026 B2
(45) Date of Patent: Aug. 17, 2010

(54) AMINOALKYL-CONTAINING GUAR DERIVATIVES

(75) Inventors: Carsten Hüttermann, Braunschweig (DE); Meinolf Brackhagen, Walsrode (DE); Jürgen Engelhardt, Bad Fallingbostel (DE)

(73) Assignee: Dow Global Technologies Inc.

( * ) Notice: Subject to any disclaimer, the term of this patent is extended or adjusted under 35 U.S.C. 154(b) by 4 days.

(21) Appl. No.: 11/446,638

(22) Filed: Jun. 5, 2006

(65) Prior Publication Data

US 2006/0287516 A1    Dec. 21, 2006

(30) Foreign Application Priority Data

Jun. 15, 2005  (DE) .................... 10 2005 027 498

(51) Int. Cl.
*C08B 37/00*    (2006.01)
(52) U.S. Cl. ........................... 536/114; 536/124
(58) Field of Classification Search ............... 536/114
See application file for complete search history.

(56) References Cited

U.S. PATENT DOCUMENTS

| 2,813,093 | A | * | 11/1957 | Caldwell et al. ............... 536/50 |
| 3,498,912 | A | | 3/1970 | Kieper et al. |
| 4,129,722 | A | | 12/1978 | Iovine et al. |
| 4,276,414 | A | | 6/1981 | Tessler |
| 4,298,494 | A | * | 11/1981 | Parslow et al. ............... 510/121 |
| 4,940,785 | A | | 7/1990 | Stober et al. |
| 5,227,481 | A | * | 7/1993 | Tsai et al. ................... 536/18.7 |
| 5,378,830 | A | * | 1/1995 | Yeh ............................. 536/118 |
| 5,739,304 | A | * | 4/1998 | Doenges et al. ............ 536/18.7 |
| 2001/0051143 | A1 | | 12/2001 | Cottrell et al. |

FOREIGN PATENT DOCUMENTS

| DE | 28 40 011 | 6/1979 |
| EP | 0 175 113 | 3/1986 |
| EP | 0 310 787 | 4/1989 |
| WO | WO 2006/010470 | 2/2006 |

OTHER PUBLICATIONS

U.S. Appl. No. 11/184,626, Wolff Cellulosics GmbH & Co. KG.

* cited by examiner

*Primary Examiner*—Shaojia Anna Jiang
*Assistant Examiner*—Jonathan S Lau

(57) ABSTRACT

A process for producing aminoalkyl-containing guar derivative is disclosed. The process entails a) dispersing a member selected from the group consisting of guar and guar derivative in a mixture of a water-miscible aprotic solvent and water and b) alkalizing the member with a base to obtain a mixture containing an alkalized member and c) etherifying the mixture with an amino-containing reagent to obtained an etherified mixture and d) optionally neutralizing the etherified mixture to obtain a material system containing a reaction product and e) optionally filtering the material system to obtain the reaction product and f) optionally washing the reaction product and g) optionally drying the reaction product referred to in f) and h) optionally grinding the reaction product. The product thus obtained is suitable for producing hair conditioners and flocculation aids.

2 Claims, 1 Drawing Sheet

AMINOALKYL-CONTAINING GUAR DERIVATIVES

FIELD OF THE INVENTION

The invention relates to aminoalkyl-containing guar derivatives and to a process for their preparation.

BACKGROUND OF THE INVENTION

Cationic and amino-containing polysaccharides may be used in many ways, e.g. as paper additives, as chelating agents and flocculating agents or as conditioners for hair. In particular, chitosan, 2-amino-2-deoxycellulose, has broad possibilities for use, inter alia as acid-stable thickener in cosmetic preparations. The isolation of this natural polysaccharide, however, is a complex process which is reflected in high prices for the products. The high price to date counteracts broad use of these polysaccharides and polysaccharide derivatives.

For the prior art, some possibilities are already known for producing aminoalkyl-containing guar derivatives.

EP 0 175 113 A2 describes polysaccharide derivatives produced by reacting polysaccharides or polysaccharide derivatives with acetal-containing substances. For example, as polysaccharide derivative base, use is made of diethylaminoethylguar having a low degree of substitution (DS 0.12). No statements are made on the properties of the diethylaminoethylguar.

DE 28 40 011 describes a process for producing diethylaminoethylguar which is characterized in that the aqueous reaction phase is emulsified in a water-immiscible solvent with addition of a surfactant. The process has the disadvantage that considerable amounts of surfactant are used. The products claimed by the process have the disadvantage that they have a lower molecular weight and a substantially lower viscosity than the inventive products.

In U.S. Pat. No. 4,276,414, in Example 4 the reaction of guar with 0.04 mol of diethylaminoethyl chloride per mole of anhydrosugar in aqueous isopropanol is described. However, no statements are mentioned as to the properties of this low-substituted diethylaminoethylguar.

U.S. Pat. No. 3,498,912 describes the production of alkylaminoalkylguar for treating wastewater. Preference here is given to the reactions of guar with amines which contain epoxy or halohydrin ($XCH_2$—CH(OH)—R) groups. They have a degree of substitution DS(N) of 0.01 to 0.5. Higher degrees of substitution are relatively difficult to achieve and are not preferred. The alkylaminoalkylguar is produced in an alcoholic solvent.

US 2001/0051143 A1 discloses cationically modified guar having a DS of 0.25 to 1.0 which is obtained by reaction in an alcoholic medium.

The previously known processes and their products, however, have some deficiencies. For instance, the known processes lead, in particular, to products which are not completely soluble and which, for a given starting viscosity, have for many applications too low a final viscosity (and correspondingly low molecular weight). A high molecular weight is of importance for many applications in which cationic polysaccharides may be used. Examples of these are wastewater clarification or hair conditioning.

SUMMARY OF THE INVENTION

A process for producing aminoalkyl-containing guar derivative is disclosed. The process entails a) dispersing a member selected from the group consisting of guar and guar derivative in a mixture of a water-miscible aprotic solvent and water and b) alkalizing the member with a base to obtain a mixture containing an alkalized member and c) etherifying the mixture with an amino-containing reagent to obtain an etherified mixture and d) optionally neutralizing the etherified mixture to obtain a material system containing a reaction product and e) optionally filtering the material system to obtain the reaction product and f) optionally washing the reaction product and g) optionally drying the reaction product referred to in f) and h) optionally grinding the reaction product. The product thus obtained is suitable for producing hair conditioners and flocculation aids.

DETAILED DESCRIPTION OF THE INVENTION

Figure 1:
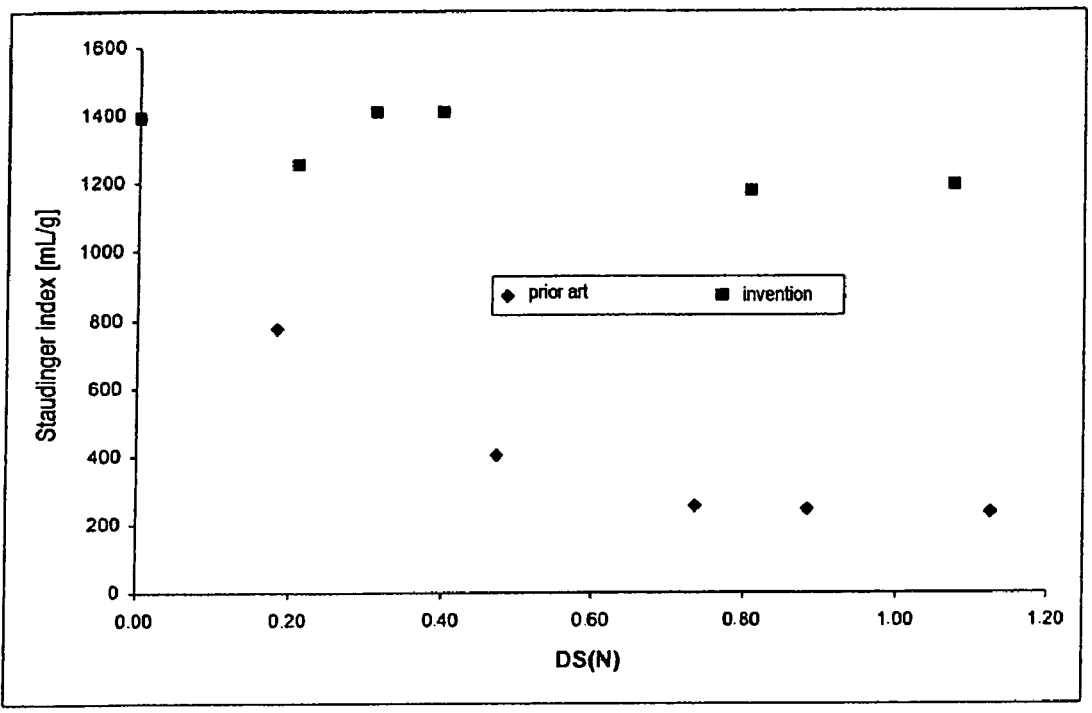
FIG. 1 compares the inventive diethylaminoethylguar to corresponding guars differently prepared in terms of their Staudinger indices.

It was an object of the invention, therefore, to develop inexpensive high-viscosity amino-containing high-molecular-weight polysaccharide derivatives which are completely water soluble even at a low degree of substitution.

It has now been found that by means of the etherification described hereinafter of guar or guar derivatives with aminoalkyl chlorides, e.g. diethylaminoethyl chloride hydrochloride (DEC) in a slurry process, dialkylaminoalkylguar may be produced at surprisingly high yield.

The products may be purified with little effort and have the following advantages compared with the prior art:
1) These amino-containing polysaccharide derivatives dissolve excellently in cold water yielding a solution of high clarity.
2) The products have a high molecular weight.
3) The aqueous solutions have a high viscosity.

The invention relates to a process for producing aminoalkyl-containing guar derivatives, characterized in that
a) Guar or a guar derivative is dispersed in a mixture (slurry) of a water-miscible aprotic solvent and water and
b) the guar or guar derivative is alkalized by a base and
c) an etherification is then carried out using an amino-containing reagent if appropriate at elevated temperature and then
d) if appropriate the mixture is neutralized and
e) the reaction product if appropriate is filtered off, if appropriate washed, if appropriate dried and if appropriate ground.

Guar is a meal which is obtained by grinding the endosperm of the seeds of the plant *Cyamopsis tetragonolobus* which is indigenous to India. The main constituent of guar is guaran, a nonionogenic polysaccharide of β-(1→4)-glycosidically linked D-mannopyranose units having α-(1→6)-linked D-galactopyranose in the side chain, more precisely one D-galactose unit per 2 mannose units.

Instead of guar, guar derivatives, in particular guar ethers may also be used. Examples of guar ethers are hydroxypropylguar, hydroxyethylguar, methylguar, carboxymethylguar or guar ethers having mixed substituents, for example hydroxypropylmethylguar or hydroxyethylmethylguar.

For the slurry medium (slurry=solvent+water), those solvents are used which are water-miscible and aprotic. These are preferably ketones or ethers. Particularly preferred solvents are acetone, methyl ethyl ketone, dimethoxyethane. Very particular preference is given to dimethoxyethane.

The fraction of solvent in the slurry medium should be high enough so that the water-soluble guar or guar derivative is not dissolved but dispersed. Likewise, the fraction of water in the slurry medium should be high enough so that the base is at least partially dissolved in the slurry medium in the alkalization. A solvent fraction in the slurry medium of 40-90% is preferred.

The reaction is carried out in a stirred vessel or reaction mixer in the presence of a water-miscible aprotic solvent. The reaction may be carried out in a stirred vessel if the ratio of polysaccharide to slurry is up to approximately 1:5, preferably about 1:15 to 1:6 parts by weight. At higher ratios of up to about 1:4 parts by weight, the batch may become more difficult to stir. In this case, a reaction mixer may be used. These are offered, e.g. under the name All In One Reactor® (Gebr. Lödige Maschinenbau, Division Drais, Mannheim) or under the name DRUVATHERM® Reactor (Gebr. Lödige Maschinenbau, Paderborn). These mixers generally include a horizontally arranged usually cylindrical mixing chamber. In this is situated a shaft which is provided, e.g. with paddle-shaped or ploughshare-shaped mixing elements. When the shaft rotates, particles are ejected from the bed of material to be mixed and vortexed and mixed in the space above the material to be mixed. The mixer may if appropriate be provided with further internals, for example what are termed knife heads or nozzles. [Karl Sommer in: "Mixing of Solids, 3. Designs of Solid—Solid Mixers, 3.3 Paddle Mixers", Ullmann's Encyclopedia of Industrial Chemistry, Wiley-VCH Verlag GmbH & Co. KgaA, 2002. DOI: 10.1002/14356007.b02_27, Article Online Posting Date: Jun. 15, 2000].

The guar or guar derivative, before addition of the amino-containing reagent, is mixed with a base, preferably an alkali metal hydroxide or alkaline earth metal hydroxide, particularly preferably sodium hydroxide. The sequence of the addition, however, may also be reversed. The base may be added in solid form or in the form of a solution. If exclusively solid bases are used, if appropriate some water must be added, since a certain amount of water must be present in the system during the alkalization.

When the free amine is used, acid formed during the etherification may be bound by the amino group. However, preferably at least 0.5 equivalents of base per mole of amine should be used, particularly preferably at least 0.7 equivalents, in order to achieve a sufficient reaction rate.

At most 1.5 equivalents of base should be used per mole of amine, preferably at most 1.2 mol and in a particularly preferred embodiment, 0.8-1.1 mol.

The amount of base must be increased correspondingly, if the amino-containing reagent is used in the form of an ammonium salt, e.g. as hydrochloride. Then, in addition, at least an equimolar amount, based on the ammonium salt, of base must be added in order to release the amine, e.g. from the hydrochloride.

Suitable compounds as amino-containing reagent are compounds of the general formula

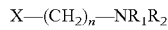

where

X is a leaving group, preferably chlorine, bromine, iodine or a sulphonic acid radical R'SO$_3$, where R' is an aromatic or aliphatic radical, e.g. para-toluyl or methyl, X is preferably chlorine, however, and n must be at least 2, the radicals R$_1$ and R$_2$, each of which is optionally substituted by heteroatoms, are independently of one another aliphatic or branched or cyclic alkyl or aryl substituents having 1-24 carbon atoms, or H. Two radicals R$_1$ and R$_2$ together with the nitrogen atom may form a ring.

Examples of amino-containing reagents to be used according to the invention are N-(2-chloroethyl)-N,N-diisopropylamine, N-(2-chloroethyl)-N,N-diethylamine, N-(3-chloropropyl)-N,N-dimethylamine, N-(3-chloropropyl)-N,N-diethylamine, N-(2-chloroethyl)-N,N-dimethylamine and N-(2-chloropropyl)-N,N-dimethylamine. The radicals R$_1$ and R$_2$ can, together with the nitrogen, form a cyclic radical. Examples of inventively used amino-containing reagents in which two radicals R$_1$ and R$_2$ together with the nitrogen form a ring are N-(2-chloroethyl)pyrrolidine, N-(2-chloroethyl)piperidine and N-(2-chloroethyl)morpholine. The amino-containing reagents may be used in the form of the ammonium salts, e.g. a hydrochloride. Not only the solid, but also a solution of, e.g. 65% by weight or 50% by weight in water or another solvent may be used.

Preferably, use is made of N-(2-chloroethyl)-N,N-diisopropylamino, N-(2-chloroethyl)-N,N-diethylamine hydrochloride or N-(2-chloroethyl)-N,N-dimethylamine hydrochloride.

Per mole of anhydrosugar, use is made of about 0.1-3 mol, preferably about 0.1-2 mol, particularly preferably about 0.3-1.5 mol, of amino-containing reagent.

The reaction is preferably carried out at temperatures of 40° C. to about 90° C., particularly preferably 60° C. to about 75° C. The reaction time depends on the reactor and the amount of amino-containing reagent used and is preferably 30 minutes to 4 hours, particularly preferably 2 to 4 hours.

After the reaction, the product may be freed from salts and byproducts, e.g. by filtration. For this, addition of acids such as formic acid, acetic acid, hydrochloric acid or sulfuric acid may be carried out before or after the filtration. The filtercake may be washed with a suitable wash medium. Suitable wash media include, in addition to the wash-miscible aprotic solvents, alcohols, for example isopropanol, ethanol or methanol, or ketones, for example acetone, and their mixtures with water. A preferred wash medium is an isopropanol-water-mixture in the ratio isopropanol:water 3:2 to 9:1. However, it is also possible not to remove the byproducts and to use the product in unpurified form for technical applications.

The product isolated from the reaction medium may be purified and dried and optionally ground. For this, commercially conventional apparatuses may be used.

The yield is calculated here in accordance with the formula mentioned in EP-A 0 310 787:

$$\text{Yield (in \%)} = DS_{theor.}/DS_{mes.}$$

$DS_{theor.}$=theoretically possible degree of substitution DS, calculated from the molar ratio of amino-containing reagent to anhydrosugar $DS_{mes.}$=measured DS, calculated from the formula $$DS_{mes.} = \frac{\%N \cdot M_{PS}}{(14 \cdot 100) - (\%N \cdot (M_{V_e} - 1))} \text{ where}$$

$M_{PS}$=molecular weight of a monomer unit of guar in g/mol
%N=measured nitrogen value in % by weight, based on dry product
$M_{V_e}$=molecular weight of the amino-containing reagent in g/mol This formula, however, only gives exact values when the nitrogen content only relates to the amino-containing polysaccharide. The values reported after nitrogen determination (by Kjeldahl), however, are based on the total mass, if appropriate corrected for the moisture. A more exact $DS_{mes.}$ is calculated when the nitrogen value is based on active content, i.e. the measured nitrogen content is corrected for the acids and salts still present:

$$DS_{mes.} = \frac{\%N \cdot M_{PS} \cdot \frac{Ac}{100}}{(14 \cdot 100) - \left(\%N \cdot \frac{Ac}{100} \cdot (M_{V_e} - 1)\right)}$$

where Ac=active content, based on the total dry mass in %

Using the inventive process, amino-containing guar derivatives may be produced in simple, widely available plants and in high yield. Likewise, the reactions may be carried out with a high consistency. The addition of surfactants which must then be removed from the product is avoided. A further advantage is the simple purification of the guar derivatives. The products may readily be separated off from the slurry medium by filtration and purified heterogeneously.

The products of the inventive process which are a further subject matter of the present invention are guar derivatives in which some of the hydroxyl groups have been converted to dialkylaminoalkyl ether groups of the general formula O—(CH$_2$)$_n$—NR$_1$R$_2$, 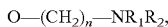

where
n must be at least 2,
the radicals R$_1$ and R$_2$, each of which is optionally substituted by heteroatoms, are independently of one another aliphatic or branched or cyclic alkyl or aryl substituents or H. Two radicals R$_1$ and R$_2$ together with the nitrogen atom may form a ring.

The nitrogen of the substituents may also be present in quaternized form, e.g. by a further reaction with the amino-containing reagent.

The inventive guar derivatives have, for the same molecular weight as the starting material, higher molecular weights than those which have been produced by the prior art. This may be read off from the Staudinger indices of the inventively produced guar derivatives compared with those products which have been produced by the emulsion process which is described in DE 2 840 011.

A high molecular weight is of importance for many applications in which cationic polysaccharides may be used. Examples of these are wastewater clarification or hair conditioning.

The inventively produced dialkylaminoalkylguar derivatives in addition have, compared with guar derivatives which have been produced by the prior art, a high viscosity at a high clarity of solution.

The inventively produced products may be used, for example, as hair conditioner in shampoos, or as an additive in cosmetic products, for example soaps, creams, lotions or skin or face cleansers. Likewise, they may be used as flocculation aids for example in wastewater clarification. These applications of the inventive dialkylaminoalkylguar derivatives form a further subject matter of the present invention.

The invention is to be described in more detail by the examples hereinafter, but without being restricted to these examples.

EXAMPLES

The DS reported is based on pure dialkylaminoethylguar, i.e. the total amount was corrected for the water content, the chloride ion content and also the sodium ion content. The sodium ion content was determined from the sulphate ash assuming that this consisted 100% of Na$_2$SO$_4$.

The Staudinger indices were determined by viscosity measurements in a capillary viscosimeter according to Ubbelohde at 20° C. in 0.1 M NaCl solution. The statistical evaluation was performed using the method of Huggins.

The charge density relates to the number of quaternized amino groups and was determined by polyelectrolyte titration against polyethenesulphonic acid sodium salt at pH 11.5.

The chemicals were obtained commercially. The nitrogen content was determined by the Kjeldahl method and based on a duplicate determination of the sample. The viscosities were determined in a solution of 2% by weight of the polymer at a shear gradient of 2.55 s$^{-1}$ using a Rotovisko VT 550 rheometer, from Haake.

Examples 1-6

Production of Diethylaminoethylguar in a Water-Dimethoxyethane Slurry

Guar (53 g, dry content 92.18%, Staudinger index: 1392 ml/g) is suspended in a mixture of dimethoxyethane (647.8 g) and water (96.3 g) in a 1 L glass four-neck ground-glass joint round-bottomed stirring apparatus having an impeller agitator.

The specified amount of sodium hydroxide is added as solid and, after 1 h at room temperature, the specified amount of N-(2-chloroethyl)-N,N-diethylamine hydrochloride is added as aqueous solution (65% by weight) and the reaction mixture is heated to 60° C. under a nitrogen atmosphere. After a reaction time of 4 h, the batch is allowed to cool and neutralized with hydrochloric acid (19% by weight) to pH 6-7. The product is repeatedly washed with 80% strength aqueous isopropanol and finally pure acetone, dried and ground.

| Batch | Example 1 | Example 2 | Example 3 |
|---|---|---|---|
| NaOH, g | 5.3 | 7.9 | 10.6 |
| N-(2-chloroethyl)-N,N-diethylamine hydrochloride (65% by weight), g | 15.9 | 23.8 | 31.8 |
| Crude yield, g | 49.9 | 55.0 | 58.1 |
| Dry content, % | 96.53 | 97.03 | 96.6 |
| Nitrogen content, % based on dry mass | 1.55 | 2.16 | 2.61 |
| DS | 0.21 | 0.31 | 0.4 |
| Charge density at pH 11.5, mmol/g | 0 | 0.16 | 0.18 |

| Batch (continued) | | | |
|---|---|---|---|
| Conversion rate based on diethylaminoethyl chloride hydrochloride, % | 100 | 100 | 99 |
| Sulphate ash, % based on dry mass | 1.83 | 1.43 | 1.35 |
| Chloride content, % based on dry mass | 2.35 | 3.63 | 5.1 |
| Viscosity (2% by weight in water), mPa·s | 51800 | 39830 | 33060 |
| Turbidity (1% by weight in water), NTU | 41.7 | 18.4 | 13.3 |
| Transmission (1% by weight in water), % | 58.8 | 77 | 82.1 |
| Staudinger index, ml/g | 1256 | 1411 | 1410 |

| Batch | Example 4 | Example 5 | Example 6 |
|---|---|---|---|
| NaOH, g | 13.2 | 26.4 | 39.6 |
| N-(2-chloroethyl)-N,N-diethylamine hydrochloride (65% by weight), g | 39.7 | 79.4 | 119.2 |
| Crude yield, g | 39.6 | 58.5 | 73.1 |
| Dry content, % | 96.7 | 96.8 | 96.0 |
| Nitrogen content, % based on dry mass | 2.9 | 4.2 | 4.9 |
| DS | 0.5 | 0.8 | 1.1 |
| Charge density at pH 11.5, mmol/g | | 0.31 | 0.31 |
| Conversion rate based on diethylaminoethyl chloride hydrochloride, % | 90 | 81 | 72 |
| Sulphate ash, % based on dry mass | 1.1 | 0.7 | 0.6 |
| Chloride content, % based on dry mass | 5.4 | 9.0 | 11.8 |
| Viscosity (2% by weight in water), mPa·s | 27660 | 15350 | 12750 |
| Turbidity (1% by weight in water), NTU | 10.7 | 5.6 | 4.5 |
| Transmission (1% by weight in water), % | 86.0 | 92.1 | 93.2 |
| Staudinger index, ml/g | | 1177 | 1198 |

Comparative Examples 1-5

Production of Diethylaminoethylguar in a Water-in-Oil Emulsion According to DE 2840011

Guar (61 g, dry content 92.18%, Staudinger index: 1392 ml/g) is suspended in a mixture of octane (200 g) and Brij 92 (20 g) in a 500 L glass four-neck ground-glass joint round-bottomed stirring apparatus having an impeller agitator.

The specified amount of N-(2-chloroethyl)-N,N-diethylamine hydrochloride is added as aqueous solution (65% by weight). The specified amount of sodium hydroxide is then added as 50% strength aqueous solution in the course of 45 minutes. The reaction mixture is heated to 70° C. under a nitrogen atmosphere. After a reaction time of 4 h, the batch is allowed to cool and is neutralized using concentrated hydrochloric acid to pH 4.5. The product is repeatedly washed with 80% strength aqueous isopropanol and finally pure acetone, dried and ground.

| Batch | Comparison 1 | Comparison 2 | Comparison 3 |
|---|---|---|---|
| NaOH solution (50% by weight), g | 17.7 | 29.01 | 46.41 |
| N-(2-chloroethyl)-N,N-diethylamine hydrochloride (65 wt-%), g | 26.7 | 46.3 | 74.1 |
| Crude yield, g | 30.3 | 37.3 | 47.8 |
| Dry content, % | 95.6 | 96.39 | 95.46 |
| Nitrogen content, % based on dry mass | 1.4 | 2.93 | 3.77 |
| DS (N) | 0.18 | 0.47 | 0.74 |
| Charge density at pH 11.5, mmol/g | 0 | 0.21 | 0.33 |
| Conversion rate based on diethylaminoethyl chloride hydrochloride, % | 62 | 95 | 92 |
| Sulphate ash, % based on dry mass | 5.5 | 3.39 | 8.02 |
| Chloride content, % based on dry mass | 2.5 | 6.55 | 11.6 |
| Viscosity (2% by weight in water), mPa·s | 13790 | 338 | 33.6 |
| Turbidity (1% by weight in water), NTU | 81.1 | 8.3 | 6.5 |
| Transmission (1% by weight in water), % | 70.9 | 92.1 | 92.9 |
| Staudinger index, ml/g | 776 | 403 | 256 |

| Batch | Comparison 4 | Comparison 5 |
|---|---|---|
| NaOH solution (50% by weight), g | 58.01 | 87.02 |
| N-(2-chloroethyl)-N,N-diethylamine hydrochloride (65% by weight), g | 93.0 | 139.0 |
| Crude yield, g | 60.5 | 61.0 |
| Dry content, % | 90.4 | 92.5 |
| Nitrogen content, % based on dry mass | 4.18 | 5.03 |
| DS (N) | 0.88 | 1.12 |
| Charge density at pH 11.5, mmol/g | 0.38 | 0.42 |
| Conversion rate based on diethylaminoethyl chloride hydrochloride, % | 88 | 75 |
| Sulphate ash, % based on dry mass | 6.9 | 1.34 |
| Chloride content, % based on dry mass | 13.3 | 12.1 |
| Viscosity (2% by weight in 1% strength acetic acid), mPa·s | 27.6 | 31.2 |

| | | |
|---|---|---|
| Turbidity (1% by weight in 1% strength acetic acid), NTU | 12.1 | 5.6 |
| Transmission (1% by weight in 1% acetic acid), % | 88.5 | 95.7 |
| Staudinger index, ml/g | 245 | 236 |

Examples 7-9

Production of Diisopropylaminoethylguar in a Water-Dimethoxyethane Slurry

Guar (53 g, dry content 92.18%, Staudinger index: 1392 ml/g) is suspended in a mixture of dimethoxyethane (324 g) and water (94 g) in a 1 L glass four-neck ground-glass joint round-bottomed stirring apparatus having an impeller agitator.

The specified amount of sodium hydroxide is added as solid and after 1 h at room temperature, the specified amount of N-(2-chloroethyl)-N,N-diisopropylamine hydrochloride as aqueous solution (65% by weight) and the reaction mixture is heated to 60° C. under a nitrogen atmosphere. After a reaction time of 4 h, the batch is allowed to cool and is neutralized with hydrochloric acid (19% by weight) to pH 6-7. The product is washed repeatedly with 80% strength aqueous isopropanol and finally pure acetone, dried and ground.

| Batch | Example 7 | Example 8 | Example 9 |
|---|---|---|---|
| NaOH, g | 13.2 | 26.4 | 39.6 |
| N-(2-chloroethyl)-N,N-diisopropylamine hydrochloride (65% by weight), g | 46.2 | 92.4 | 138.6 |
| Crude yield, g | 68.1 | 87.5 | 77.7 |
| Dry content, % | 96.46 | 97.18 | 96.80 |
| Nitrogen content, % based on dry mass | 1.97 | 3.44 | 4.14 |
| DS (N) | 0.30 | 0.60 | 0.93 |
| Conversion rate based on diisopropylaminoethyl chloride hydrochloride, % | 68 | 88 | 77 |
| Sulphate ash, % based on dry mass | 2.27 | 1.19 | 0.40 |
| Chloride content, % based on dry mass | 4.87 | 1.19 | 10.2 |
| Viscosity (2% by weight in water), mPa·s | 28990 | 15640 | 10320 |
| Turbidity (1% by weight in water), NTU | 6.8 | 3.2 | 6.0 |
| Transmission (1% by weight in water), % | 93.3 | 98.6 | 94.5 |
| Staudinger index, ml/g | 1419 | 1252 | 963 |

Examples 10-12

Production of Dimethylaminoethylguar in a Water-Dimethoxyethane Slurry

Guar (88 g, dry content 92.18%, Staudinger index: 1392 ml/g) is suspended in a mixture of dimethoxyethane (540 g) and water (164 g) in a 1 L glass four-neck ground-glass joint round-bottomed stirring apparatus having an impeller agitator.

The specified amount of sodium hydroxide is added as solid and after 1 h at room temperature the specified amount of N-(2-chloroethyl)-N,N-dimethylamine hydrochloride is added as aqueous solution (65% by weight) and the reaction mixture is heated to 60° C. under a nitrogen atmosphere. After a reaction time of 4 h, the batch is allowed to cool and is neutralized with hydrochloric acid (19% by weight) to pH 6-7. The product is washed repeatedly with 80% strength aqueous isopropanol and finally pure acetone, dried and ground.

| Batch | Example 10 | Example 11 | Example 12 |
|---|---|---|---|
| NaOH, g | 22 | 44 | 66 |
| N-(2-chloroethyl)-N,N-dimethylamine hydrochloride (65% by weight), g | 55.4 | 110.8 | 166.2 |
| Crude yield, g | 87.0 | 99.0 | 94.1 |
| Dry content, % | 96.79 | 96.48 | 96.66 |
| Nitrogen content, % based on dry mass | 2.2 | 3.38 | 3.99 |
| DS (N) | 0.3 | 0.5 | 0.66 |
| Conversion rate based on dimethylaminoethyl chloride hydrochloride, % | 61 | 50 | 44 |
| Sulphate ash, % based on dry mass | 1.52 | 1.39 | 1.06 |
| Chloride content, % based on dry mass | 4.40 | 4.63 | 9.44 |
| Viscosity (2% by weight in water), mPa·s | 32630 | 23200 | 15840 |
| Turbidity (1% by weight in water), NTU | 13.6 | 7.6 | 4.5 |
| Transmission (1% by weight in water), % | 83.5 | 91.7 | 95.7 |
| Staudinger index, ml/g | 1383 | 1326 | 1209 |

Comparative Examples 6-8

Production of Diethylaminoethylguar in a Water-Isopropanol Slurry

Guar (53 g, dry content 92.18%, Staudinger index: 1392 ml/g) is suspended in a mixture of isopropanol and water in accordance with the quantity data listed below in a 1 L glass four-neck ground-glass joint round-bottomed stirring apparatus having an impeller agitator.

26.4 g of sodium hydroxide are added as solid and after 1 h of stirring at room temperature, 79.4 g of N-(2-chloroethyl)-N,N-diethylamine hydrochloride solution (65% by weight) are added and the reaction mixture is heated to 60° C. under a nitrogen atmosphere. After a reaction time of 4 h, the batch is allowed to cool and is neutralized with hydrochloric acid (19% by weight) to pH 6-7. The product is washed repeatedly with 80% strength aqueous isopropanol and finally pure acetone, dried and ground.

| Batch | Comparison 6 | Comparison 7 | Comparison 8 |
|---|---|---|---|
| Isopropanol | 648 | 686 | 724 |
| Water | 83 | 44 | 6 |
| Crude yield, g | 37.5 | 37.1 | 30.1 |
| Dry content, % | 95.9 | 95.6 | 96.1 |
| Nitrogen content, % based on dry mass | 0.75 | 0.56 | 0.58 |
| DS (N) | 0.09 | 0.07 | 0.07 |
| Conversion rate based on diethylaminoethyl chloride hydrochloride, % | 9.4 | 6.9 | 7.2 |
| Sulphate ash, % based on dry mass | 2.17 | 2.24 | 3.32 |
| Chloride content, % based on dry mass | 1.57 | 0.99 | 1.42 |
| Viscosity (2% by weight in water), mPa·s | 50250 | 37190 | 53810 |
| Turbidity (1% by weight in water), NTU | 124 | 180 | 119 |
| Transmission (1% by weight in water), % | 42.9 | 32.4 | 36.8 |

FIG. 1 shows a comparison of the Staudinger indices in 0.1 M NaCl between diethylaminoethylguar, prepared by the inventive slurry process (Examples 1 to 6, squares) and the known emulsion process according to DE 2 840 011 (Comparative Examples 7 to 11, diamond).

The diethylaminoethylguars produced by the emulsion process show a marked decrease in the Staudinger index with increasing degree of substitution. In contrast thereto, aminoalkylguar derivatives may be produced by the novel process which have high Staudinger indices and thus high molecular weights even at a high degree of substitution. As becomes clear in the diagram, the Staudinger indices do not decrease at all, or only slightly, with increasing degree of substitution.

Figure 2:
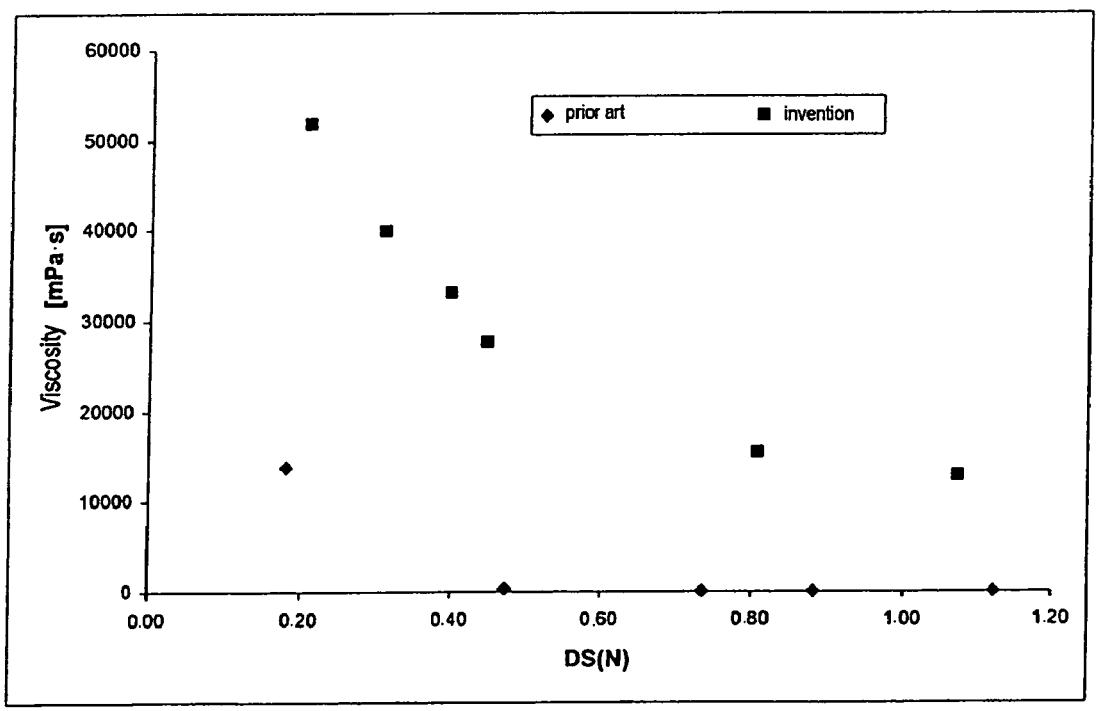
FIG. 2 compares the inventive diethylaminoethylguar to corresponding guars differently prepared in terms of their viscosities as function of the degree of substitution.

FIG. 2 shows the viscosities in water (2% by weight) of inventively produced diethylaminoethylguar (Examples 1 to 6, squares) as a function of the degree of substitution DS(N) (average number of amino groups per anhydrosugar unit). For comparison, those guar derivatives are also listed which were produced by the abovementioned emulsion process (Comparative Examples 7 to 11, diamond).

Although the invention has been described in detail in the foregoing for the purpose of illustration, it is to be understood that such detail is solely for that purpose and that variations may be made therein by those skilled in the art without departing from the spirit and scope of the invention except as it may be limited by the claims.

What is claimed is:

1. An aminoalkyl-containing guar ether, wherein the guar ether has:
   a viscosity of at least 20,000 mPa·s in a 2% solution by weight in water at a shear gradient of 2.55 s$^{-1}$;
   a DS(N)>0.3; and
   at least one aminoalkyl ether group of the formula:

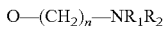

wherein:
   n is an integer greater than 1, and
   $R_1$ and $R_2$, independently of one another are H, a $C_{1-24}$ radical, or cooperate together with the nitrogen to which they are attached to form a pyrrolidine, piperidine or morpholine ring or a hydrochloride thereof.

2. A quaternized aminoalkyl-containing guar ether of claim 1, wherein at least one of said aminoalkyl ether group is quaternized and of the formula:

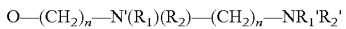

wherein:
   n is, at each occurrence, an integer greater than 1, and
   $R_1$ and $R_2$, independently of one another are H or a $C_{1-24}$ radical, and
   $R_1'$ and $R_2'$, independently of one another are H, a $C_{1-24}$ radical, or cooperate together with the nitrogen to which they are attached to form a pyrrolidine, piperidine or morpholine ring or a hydrochloride thereof.

* * * * *